United States Patent
Olivieri et al.

(10) Patent No.: US 10,045,684 B2
(45) Date of Patent: Aug. 14, 2018

(54) DISTAL SCANNING MODULE, IN PARTICULAR TO CONTROL THE AIMING AND THE MOVEMENT OF AN OPTICAL APPARATUS OF A MEDICAL DEVICE, SUCH AS A DIAGNOSTIC OR SURGICAL INSTRUMENT

(71) Applicant: FONDAZIONE ISTITUTO ITALIANO DI TECNOLOGIA, Genoa (IT)

(72) Inventors: Emidio Olivieri, Acquaviva Picena (IT); Darwin Caldwell, Serra Ricco (IT); Leonardo De Mattos, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 191 days.

(21) Appl. No.: 15/037,631

(22) PCT Filed: Nov. 18, 2014

(86) PCT No.: PCT/IB2014/066127
§ 371 (c)(1),
(2) Date: May 18, 2016

(87) PCT Pub. No.: WO2015/075628
PCT Pub. Date: May 28, 2015

(65) Prior Publication Data
US 2016/0287056 A1 Oct. 6, 2016

(30) Foreign Application Priority Data

Nov. 20, 2013 (IT) .............................. TO2013A0943

(51) Int. Cl.
*A61B 1/00* (2006.01)
*A61B 1/04* (2006.01)
(Continued)

(52) U.S. Cl.
CPC ........ *A61B 1/00098* (2013.01); *A61B 1/0057* (2013.01); *A61B 1/00172* (2013.01);
(Continued)

(58) Field of Classification Search
CPC ....... A61B 1/00098; A61B 1/063; A61B 1/07; A61B 1/04; A61B 1/0057; A61B 1/018;
(Continued)

(56) References Cited

U.S. PATENT DOCUMENTS 5,910,129 A * 6/1999 Koblish ............. A61B 18/1492
604/159
6,332,880 B1 12/2001 Yang et al.
(Continued)

FOREIGN PATENT DOCUMENTS

EP 1695655 A1 8/2006
WO 2010/042611 A1 4/2010

OTHER PUBLICATIONS

International Search Report and Written Opinion from corresponding International Application No. PCT/IB2014/066124, dated Mar. 11, 2015.

*Primary Examiner* — Timothy J Neal
(74) *Attorney, Agent, or Firm* — Merchant & Gould P.C.

(57) ABSTRACT

A module includes an oblong structure; an optical apparatus associated with the oblong structure for facing a segment arranged inside a body cavity of a patient. An actuating device is for controlling the position of the oblong structure so as to orient the optical apparatus in the body cavity. The oblong structure has a proximal portion and an end portion, which is deformable, so as to tend to remain in and elastically return to a bent condition, in which it is normally flexed. The actuating device includes a pusher member, which moves in a guided manner relative to the oblong structure and is suited to act upon the end portion, so as to
(Continued)

angularly move it from the bent condition towards a substantially straight condition.

10 Claims, 6 Drawing Sheets

(51) Int. Cl.

| | | |
|---|---|---|
| *A61B 1/005* | (2006.01) | |
| *A61B 5/00* | (2006.01) | |
| *A61B 1/018* | (2006.01) | |
| *A61B 1/06* | (2006.01) | |
| *A61B 1/07* | (2006.01) | |
| *A61B 18/24* | (2006.01) | |
| *A61M 25/01* | (2006.01) | |
| *A61B 34/30* | (2016.01) | |
| *A61B 34/20* | (2016.01) | |
| *A61B 18/00* | (2006.01) | |
| *A61B 18/20* | (2006.01) | |

(52) U.S. Cl.
CPC ............... *A61B 1/018* (2013.01); *A61B 1/04* (2013.01); *A61B 1/063* (2013.01); *A61B 1/07* (2013.01); *A61B 5/0084* (2013.01); *A61B 18/24* (2013.01); *A61B 2018/00982* (2013.01); *A61B 2018/20357* (2017.05); *A61B 2034/2055* (2016.02); *A61B 2034/301* (2016.02); *A61B 2034/305* (2016.02); *A61M 25/0147* (2013.01)

(58) Field of Classification Search
CPC ............ A61B 1/00172; A61B 1/00183; A61B 1/0014; A61B 1/0008; A61B 1/00179; A61B 18/24; A61B 5/0084; A61B 2017/00982
See application file for complete search history.

(56) References Cited

U.S. PATENT DOCUMENTS

2006/0247619 A1  11/2006  Kaplan et al.
2007/0173757 A1   7/2007  Levine et al.
2010/0292535 A1  11/2010  Paskar

* cited by examiner

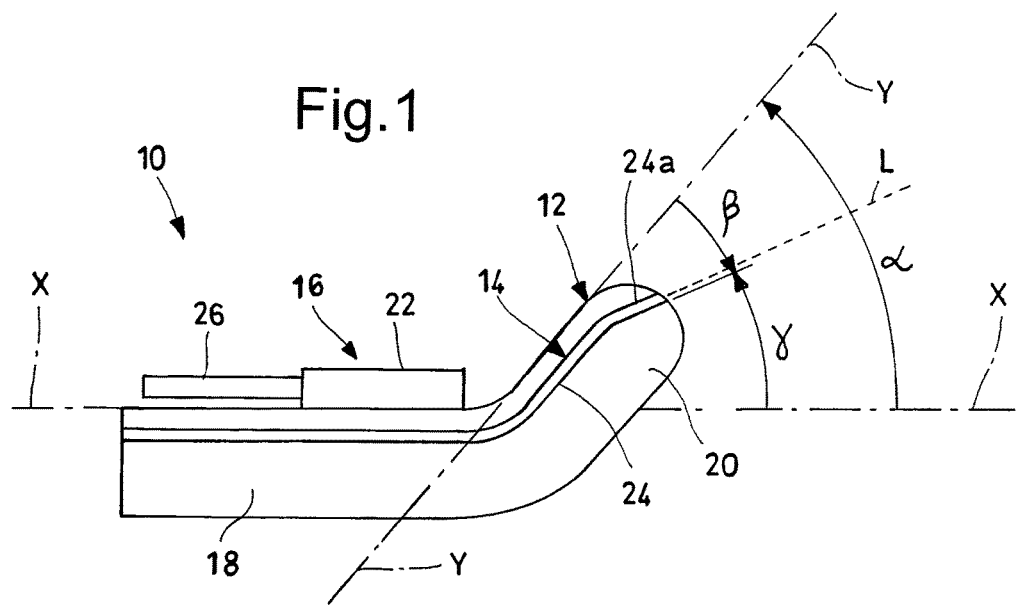
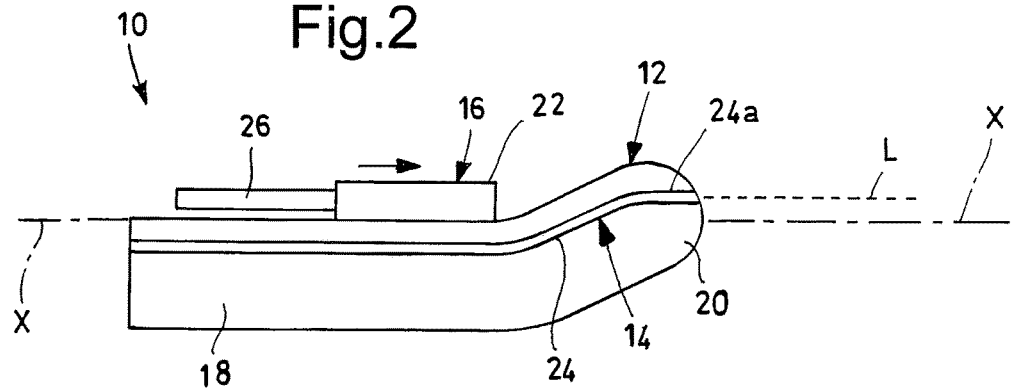
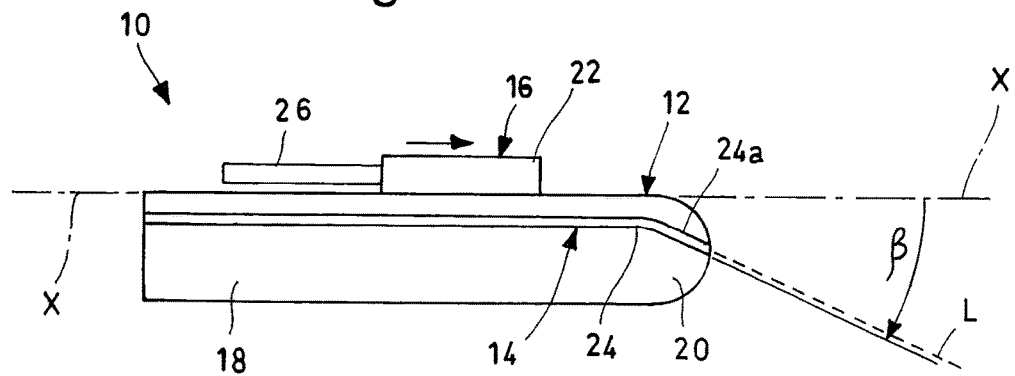

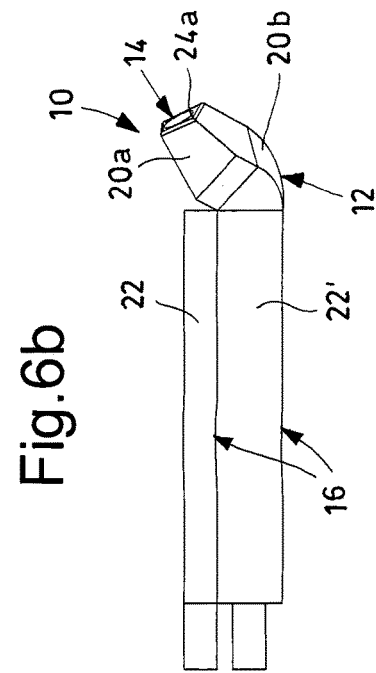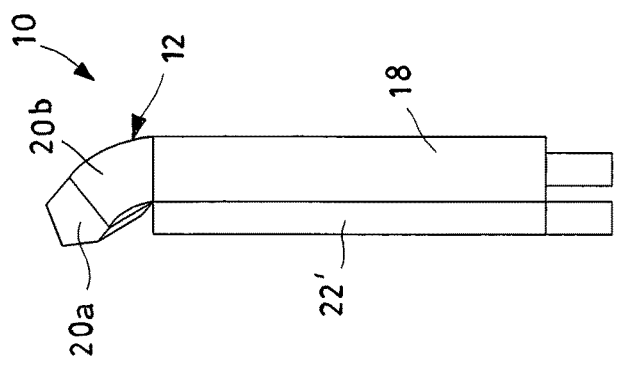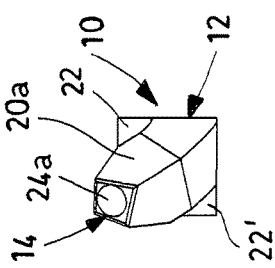

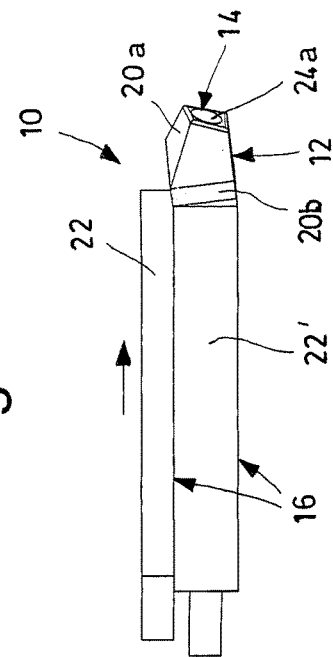
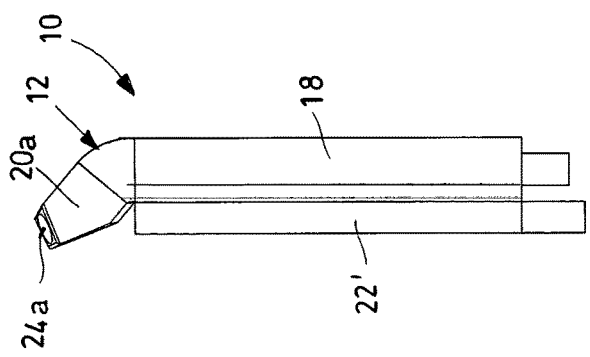
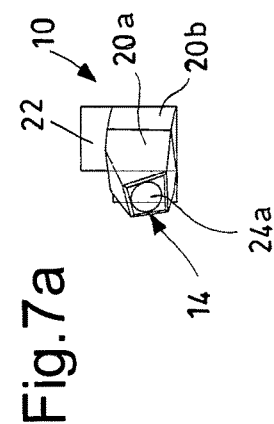

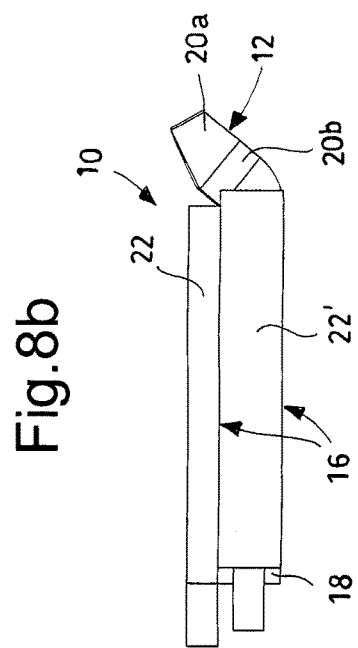
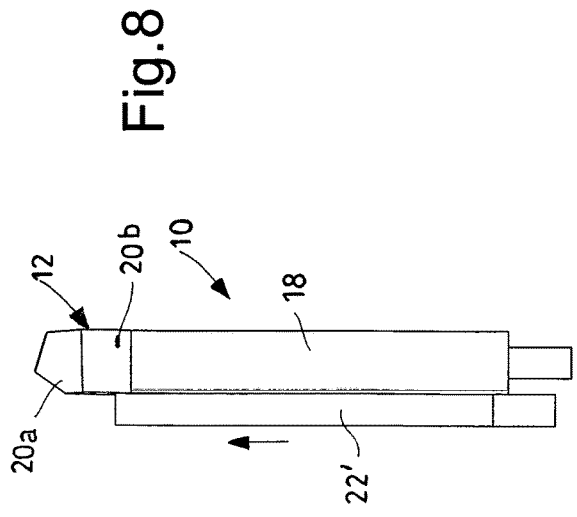
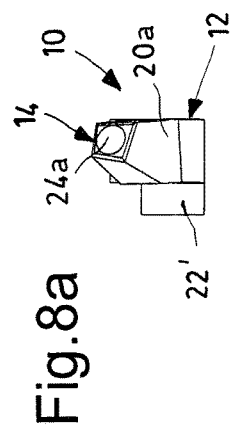

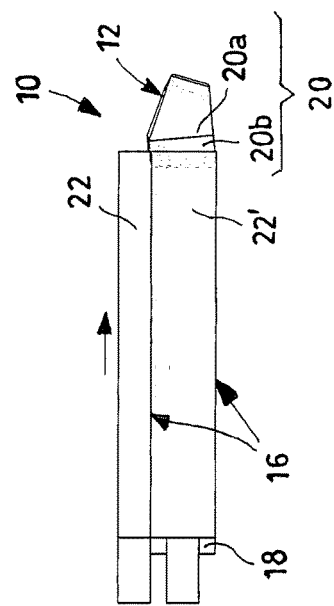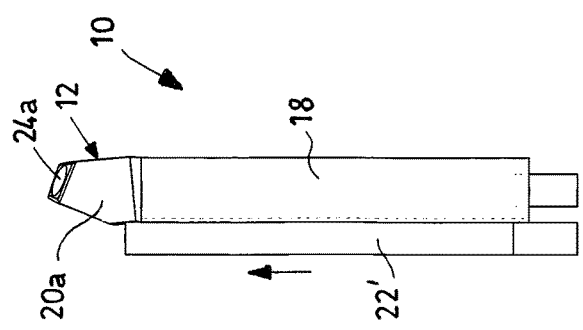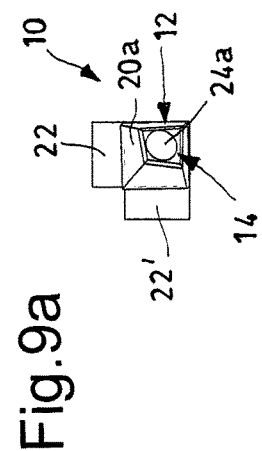

DISTAL SCANNING MODULE, IN PARTICULAR TO CONTROL THE AIMING AND THE MOVEMENT OF AN OPTICAL APPARATUS OF A MEDICAL DEVICE, SUCH AS A DIAGNOSTIC OR SURGICAL INSTRUMENT

This application is a National Stage Application of International Application No. PCT/IB2014/066127, filed 18 Nov. 2014, which claims benefit of Serial No. TO2013A000943, filed 20 Nov. 2013 in Italy and which applications are incorporated herein by reference. To the extent appropriate, a claim of priority is made to each of the above disclosed applications.

TECHNICAL FIELD

The present invention relates to a distal scanning module, in particular to control the aiming and the movement of an optical apparatus of a medical device, such as a diagnostic or surgical instrument.

TECHNOLOGICAL BACKGROUND

In the medical field—and, in particular, in the field of endoscopic laser surgery—the positioning and aiming of a laser beam are carried out by using an optical fiber moved by the surgeon, with or without robotic assistance. Therefore, laser ablation or cutting procedures are generally carried out in a "point-by-point" manner, which results in poor uniformity and precision in performing these operations.

The laser surgical systems offering the best quality results, on the other hand, typically use a scanning technology, which means that the laser beam is automatically moved along a predetermined trajectory. By employing these devices, the uniformity and homogeneity of the cuts performed using laser are high-quality, involving reduced tissue carbonization and consequently minimal thermal damage. Clearly, these aspects are extremely important and significant in surgical applications.

However, the systems adopting the above-mentioned laser scanning technology are operated from outside the patient's body and therefore require a direct line of sight from the actuation unit to the surgical site, which makes them unsuited for endoscopic surgery, unless appropriate solutions are adopted.

For this reason, in the technical field, in particular in the endoscopic field, distal modules have been adopted which can be associated with medical devices, are designed to perform different scanning operations in narrow and confined spaces and can be used either in the surgical field or simply for diagnostic purposes. For example, these distal scanning modules can be equipped, in correspondence to their tip, with an endoscopic tool designed to detect images or to aim a laser beam for the purpose of performing a tissue ablation procedure.

In this way, it is not necessary to provide a direct line of sight in surgical operations any more, because a distal scanning module of this type allows the optical detection of areas or segments of the body cavity in which the surgical operation is to be performed. Therefore, the applicability of laser technology is extended to the endoscopic field, because by using the distal scanning module it is possible to achieve a high degree of precision and minimal invasiveness.

A few prior art documents referring to the use of distal scanning modules are mentioned hereinafter.

Patent WO 2010/042611 discloses a distal scanning module. In particular, said document describes systems, devices and methods for providing insert able and adjustable robotic sensory with manipulation platforms for the so-called "single port" surgery. This invention features an insertable device that provides visual feedback upon insertion and implements a structure having a primary backbone and four secondary backbones for each of the robotic arms. It also implements a radial expansion mechanism that can separate the robotic arms. All of these elements together provide an anthropomorphic endoscopic device.

Patent EP 1 695 655 discloses a flexible tip of an endoscopic system which controls the degree of bending and which can be used for inspection and medical treatment. Said invention comprises a main tube connected to the tip and the tip comprises a working channel tube connected to the main tube. It is also provided with a bending mechanism to support and bend the working channel tube and there are one or more weights attached to the outer surface of the bending mechanism, as well as an outer skin tube to cover the outer surface of the bending mechanism together with the weights. The bending mechanism includes a coil acting as a shape-memory actuator and arranged in the longitudinal direction of the working channel tube. Thanks to this structure, it is possible to direct the active tube by driving the bending mechanism on the end side of the active tube and by bending it arbitrarily in the desired angle and direction, in order to improve the insertion ability into difficult locations.

SUMMARY OF THE INVENTION

An object of the present invention is to provide a distal scanning module which is able to solve the drawbacks of the prior art.

A further object of the present invention is to provide a distal scanning module having a simplified structure and ensuring easy and reliable operation at the same time.

Another object of the present invention is to provide a distal scanning module allowing a high degree of precision, accuracy and speed in positioning the optical apparatus associated therewith (in particular, a waveguide or an image sensor).

An additional object of the present invention is to provide a distal scanning module which is indifferently compatible with a manual or a motor-driven actuation system.

A further object of the present invention is to provide a distal scanning module which can be indifferently controlled manually or in a programmable, computer-assisted way.

Another object of the present invention is to provide a distal scanning module which is intrinsically safe, i.e. which does not comprise electrically conductive elements or moving components that can pose a potential threat by coming into contact with the patient's body.

According to the present invention, these and other objects are reached by means of a distal scanning module having the technical features set forth herein.

The appended claims are an integral part of the technical teaches provided in the following detailed description concerning the present invention. In particular, the appended claims define some preferred embodiments of the present invention and describe optional technical features.

BRIEF DESCRIPTION OF THE DRAWINGS

Further features and advantages of the present invention will be best understood upon perusal of the following detailed description, which is provided by way of example and is not limiting, with reference, in particular, to the accompanying drawings, wherein:

FIGS. 1 to 3 are lateral plan views of a distal scanning module according to an explanatory embodiment of the present invention, where said module is in different operating configurations;

FIGS. 6, 6a, 6b are orthographic projection views where the module shown in FIG. 4 is in a rest configuration;

FIGS. 7, 7a, 7b are orthographic projection views where the module shown in figures from 4 onwards is in a working condition;

FIGS. 8, 8a, 8b are orthographic projection views where the module shown in figures from 4 onwards is in a further working condition; and FIGS. 9, 9a, 9b are orthographic projection views where the module shown in figures from 4 onwards is in a further working configuration.

DETAILED DESCRIPTION OF THE INVENTION

Figure 4:
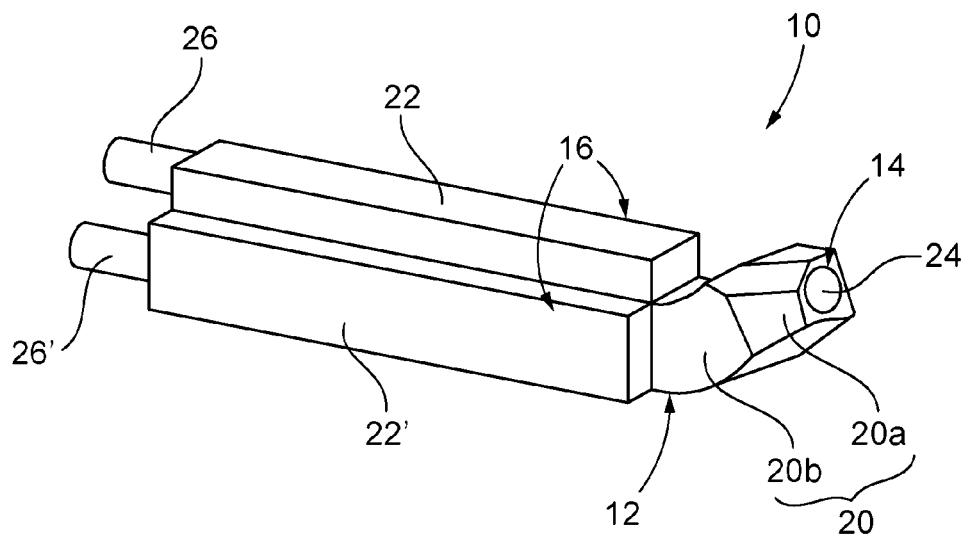
FIG. 4 is a prospective view of the distal scanning module according to an explanatory embodiment of the present invention.

With reference, in particular, to FIGS. 1 to 3, number 10 indicates, as a whole, a distal scanning module manufactured according to an explanatory embodiment of the present invention. In particular, module 10 is suited to control the aiming and the movement of an optical apparatus of a medical device, such as a diagnostic or surgical instrument. The above-mentioned embodiment is simplified, so as to make the principle underlying the present invention clear.

Module 10 comprises an oblong structure 12 and an optical apparatus 14, which is associated with the oblong structure 12 and is designed to face a segment arranged inside a body cavity of a patient; and an actuating device 16, which is designed to control the position of oblong structure 12 so as to orient optical apparatus 14 in the body cavity. Oblong structure 12 comprises a proximal portion 18 and an end portion 20, which is at least partially deformable, so as to tend to remain in and elastically return to a bent condition (shown in FIG. 1), in which end portion 20 is normally flexed, in particular transversely outwards, relative to proximal portion 18 of oblong structure 12. Actuating device 16 comprises at least one movable pusher organ 22, which is located on the outside of said oblong structure and moves in a guided manner relative to oblong structure 12 and is suited to act upon end portion 20, so as to angularly move end portion 20 from the bent condition towards a substantially straight condition (shown in FIG. 3), in which end portion 20 is caused to be aligned with proximal portion 18 of oblong structure 12.

Thanks to the features mentioned above, module 10 offers a structure which is mechanically not complex and can work in an easy, reliable way. In particular, module 10 is able to move and orient optical apparatus 14 associated therewith inside the body cavity according to at least one degree of freedom in space. At the same time, module 10 is indifferently compatible with a manual actuation system of the pusher member 22, i.e. without any input of energy (electric, hydraulic or pneumatic) from external sources in order to cause it to move, or with a motor-driven actuation system, i.e. aided by actuators or motors acting on said pusher member 22 in order to cause it to move.

In the embodiment shown in FIGS. 1 to 3, oblong structure 12 comprises a beam-shaped element, in particular having a quadrangular cross section, in which the longitudinal dimensions exceed the transverse dimensions. In particular, as mentioned above, end portion 20 is normally in the bent condition, as shown in FIG. 1.

Preferably, in the bent condition, end portion 20 and the longitudinal direction X-X defined by proximal portion 18 of oblong structure 12 form an angle α, in particular an acute angle, such as an angle greater than 45° (for example, +50°). For an observer who is looking at figures from 1 to 3, end portion 20 deviates from the longitudinal direction X-X in a counterclockwise direction.

In the figures shown by way of example and in the present description, the sign convention adopted for the angles formed relative to the longitudinal direction X-X is basically as follows:

the angle counts as positive if there is a counterclockwise deviation from the longitudinal direction X-X, and
on the contrary, the angle counts as negative if there is a clockwise deviation from the longitudinal direction X-X.

In the embodiment shown in FIG. 3, in the substantially straight condition end portion 20 is aligned with proximal portion 18, thus substantially defining a single longitudinal direction (or axis) X-X of oblong structure 12. In further embodiments, though less preferred, in said substantially straight condition end portion 20 can form a reduced angle (or at least smaller than the one corresponding to the bent condition) with the longitudinal direction (X-X) of proximal portion 18 of oblong structure 12.

Preferably, at least end portion 20 of oblong structure 12 comprises a material provided with superelastic properties. In particular, said material is of the shape-memory type, more precisely an alloy of nickel and titanium (Nitinol). Generally, materials of the shape-memory type have an elastic modulus ranging from 40 to 80 GPa and can have a resistance to tensile stress higher than 107 MPa and an overall elongation higher than 10%. For example, with these features an oblong structure 12 manufactured with a Nitinol tube having a ca. 2 mm diameter section can be bent and reach a bending of 30 mm without negatively affecting its shape and its other mechanical features.

In the embodiment shown in FIGS. 1 to 4, oblong structure 12 is entirely (i.e. both proximal portion 18 and end portion 20) made from a shape-memory material, in particular from the above mentioned alloy of nickel and titanium.

In further embodiments, oblong structure 12 can also not be manufactured monolithically from the same material; more specifically, it is possible to use a material allowing an elastic return only for end portion 20 (or even only for the part thereof which is adjacent to proximal portion 18 and upon which pusher member 22 is suited to act in order to strictly ensure the passage from the bent condition to the substantially straight condition), thus making it structurally separate from proximal portion 18.

In the embodiment shown in FIGS. 1 to 3, optical apparatus 14 comprises a waveguide 24, for example an optical fiber, which is associated with oblong structure 12. Preferably, waveguide 24 passes through oblong structure 12, in particular in a position that is eccentric thereto, extending through proximal portion 18 and distal, or end, portion 20. In other words, waveguide 24 provides an internal core around which oblong structure 12 extends.

In the embodiment shown in FIGS. 1 to 3, waveguide 24 ends, in correspondence to said end portion 20, with an optically divergent segment 24*a* that is optically divergent relative to the longitudinal direction Y-Y of end portion 20.

In particular, divergent segment 24*a* is a segment of waveguide 24 which is inclined in a direction that is opposite (in a clockwise direction for those observing the drawings) to the one in which end portion 20 deviates from proximal portion 18 of oblong structure 12. In the embodiment shown with particular reference to FIGS. 1 to 3, divergent segment 24*a* optically diverges—and in particular is inclined—by an angle β (in this case, for example, of about −20°) relative to the longitudinal direction Y-Y. More specifically, said angle β has an opposite sign to the one taken by angle α relative to the longitudinal direction X-X.

In the figures shown by way of example and in the present description, the sign convention adopted for the angles formed relative to the longitudinal direction Y-Y is substantially similar to the one adopted for the angles formed relative to the longitudinal direction X-X, i.e. the following:

the angle counts as positive if there is a counterclockwise deviation from the longitudinal direction Y-Y, and on the contrary, the angle counts as negative if there is a clockwise deviation from the longitudinal direction Y-Y.

As a person skilled in the art can clearly assume, the sign conventions chosen for the angles formed relative to the longitudinal direction X-X and for those formed relative to the longitudinal direction Y-Y have to be considered explanatory and merely aimed at making the description of the principle underlying the present invention even clearer, with particular reference to FIGS. 1-3. In any case, it remains evident that said conventions should not be interpreted as limiting for the scope of protection claimed for the present invention.

In the embodiment shown in FIGS. 1 to 3, waveguide 24 is adapted to be passed through by a light beam L, so that its movement and orientation in space is controlled by the action of pusher organ 22, which acts upon end portion 20.

In particular, light beam L passing through waveguide 24 can serve diagnostic and/or surgical purposes. By way of example, light beam L passing through waveguide 24 can be suited to allow a detection (such as an image coming from the body cavity and directed backwards by end portion 20 towards proximal portion 18 of oblong structure 12) and/or to help or allow a surgical operation to be performed (as a laser beam with an aiming or an ablation function).

Preferably, the pusher member 22 moves in a guided manner relative to proximal portion 18 of oblong structure 12.

In the embodiment shown in FIGS. 1 to 3, pusher member 22 slides along the walls of the beam-shaped element defined by oblong structure 12, in particular on proximal portion 18. Preferably, pusher member 22 slides along a rectilinear direction, in particular a direction that is parallel to the longitudinal direction X-X defined by proximal portion 18, but in other embodiments it is possible to provide other types of movement for pusher member 22 relative to oblong structure 12 (for example, a rotation or an oscillation movement).

In the embodiment shown in FIGS. 1 to 3, pusher member 22 is operatively movable between a retracted position, in which it is not in contact with (or, more generally, does not exert pressure on) end portion 20 in the bent condition, and an extended position, in which it acts upon end portion 20, thus moving it to and keeping it in the substantially straight condition. In the intermediate positions between the retracted and the extended position, pusher member 22 pushes end portion 20 to and keeps it in—countering its elastic return—an intermediate angular position relative to proximal portion 18 of oblong structure 12 between the bent condition and the substantially straight condition.

In the embodiment shown in FIGS. 1 to 3, pusher member 22 is suited to operatively act only upon a part of end portion 20, in particular only upon a segment adjacent to proximal portion 18.

As mentioned above, pusher member 22 can be adapted to be manually moved by a user, for example by acting on a rod 26 connected thereto (in particular on the longitudinally opposite side relative to end portion 20) and to be accessible also from a remote position with respect to end portion 20. Alternatively, pusher member 22 can be adapted to be moved in a controlled manner by a motor or an actuator (not shown in the drawings), for example by means of an electric motor whose electrically conductive components are preferably located in a remote position relative to module 10 and to its end portion 20.

In the embodiment shown, pusher member 22 is manufactured in the shape of a bar with at least one of its lateral faces substantially flat (or at least complementary to the sliding surface of oblong structure 12). In this way, the sliding becomes easier in case oblong structure 12, in particular in correspondence to proximal portion 18, is also beam-shaped. For example, the cross section of the bar defined by pusher member 22 can be rectangular or square.

An operating mode of module 10 according to the embodiment shown in FIGS. 1 to 3 will be described below.

As one can assume from FIGS. 1 to 3, module 10 is suited to have only one degree of freedom, namely it can rotate on a plane.

FIG. 1 shows module 10 when end portion 20 is in the bent condition and pusher member 22 is in its retracted position. Therefore, waveguide 24, in particular its divergent segment 24*a*, is inclined by an angle equal to the angular sum γ of angle α and angle β (for example, by about +30°) relative to the longitudinal direction X-X defined by proximal portion 18 of oblong structure 12. In this condition, in case light beam L is coming out of waveguide 24 relative to end portion 20, it will be emitted at an inclination angle equal to angular sum γ relative to the longitudinal direction X-X identified by proximal portion 18 of oblong structure 12. This orientation in space of module 10 and of its components corresponds to a normal or rest configuration, in which pusher member 22 is not actuated (manually and/or by motors or actuators) to act upon end portion 20, and therefore remains in its retracted position.

Now, pusher member 22 can be partially actuated from the retracted position towards the extracted position, as shown in FIG. 2.

In this situation, pusher member 22 acts upon a part of end portion 20, which is in the bent condition, and counters the elastic force exerted by end portion 20 itself, so as to angularly push it away from said bent condition. Therefore, in this step end portion 20 is in an intermediate condition between the bent (FIG. 1) and the substantially straight (FIG. 3) condition. Hence, the position assumed by waveguide 24, in particular by its divergent segment 24*a*, reduces its inclination (relative to the longitudinal direction X-X defined by proximal portion of oblong structure 12) with respect to the value of angular sum γ, reaching for example the null value specifically shown in FIG. 2. Consequently, in the condition shown in FIG. 2, in case light beam L is coming out of waveguide 24 relative to end portion 20, it will be substantially parallel to longitudinal direction X-X identified by proximal portion 18 of oblong structure 12. This orientation in space of module 10 and of its components corresponds to an operating or working configuration, in which pusher member 22 is actuated to act upon end portion 20, being and remaining in a partially extended position in order to hold end portion 20 in the desired intermediate condition by countering the elastic return.

Now, pusher member 22 can be partially actuated from the retracted position towards the extracted position and go beyond the intermediate position shown in FIG. 2 towards the extended position, which is shown in FIG. 3.

As you can see, end portion 20 ends up in a condition in which the orientation taken on by waveguide 24 (in particular by its divergent segment 24a) assumes negative inclination values relative to the longitudinal direction X-X defined by proximal portion 18 of oblong structure 12. In this embodiment, the assumed inclination value (relative to the longitudinal direction X-X) can reach the value of angle β (i.e., in this embodiment, substantially equal to −20°). Consequently, in the substantially straight condition (shown in FIG. 3) of end portion 20, in case light beam L is coming out of waveguide 24 relative to end portion 20, it will be inclined (relative to the longitudinal direction X-X) by a value corresponding to angle β. This orientation in space of module 10 and of its components corresponds to a further operating or working configuration, in which pusher member 22 is actuated to act upon end portion 20, being and remaining in a completely extended position in order to hold end portion 20 in the substantially straight condition.

Therefore, thanks to these solutions, it is possible to precisely and quickly control the position of divergent segment 24a of waveguide 24 on a plane of position, thus allowing an angular range relative to proximal portion 18 of oblong structure 12 (and therefore relative to the longitudinal direction X-X) between:

a value equal to angular sum γ (for example, +30°) and
a value equal to angle β (for example, −20°).

This situation is particularly appreciated and advantageous when waveguide 24, for example an optical fiber, is adapted to be passed through by a laser beam L acting in "scanning" mode, regardless of whether it is suited for aiming or for ablation.

With reference to FIGS. 4 to 9b, the drawings show a further explanatory embodiment of the present invention.

Details and elements that are similar to those of the embodiment described above—or fulfill a similar function—are associated with the same alphanumeric references. For the sake of brevity, the description of these details and elements will not be repeated below, but reference is made to what was explained in the description of the embodiment shown in FIGS. 1 to 3.

In particular, actuating device 16 comprises a pair of pusher member 22, 22', each of them being suited to stress end portion 20 in a flexing manner on a respective plane and to determine a respective degree of freedom of angular movement of said end portion on said plane. In the embodiment shown, the two planes on which end portion 20 can be stressed in a flexing manner are perpendicular to one another.

Preferably, the second pusher member 22' is manufactured so as to have the same characteristics of the first pusher member 22 described above in relation to the embodiment shown in FIGS. 1 to 3. Therefore, regarding the second pusher member 22', reference is made to what was previously explained in relation to the first pusher member 22.

In this way, it becomes possible to control the orientation in space of waveguide 24 based on two degrees of freedom of movement. Therefore, end portion 20 is flexible on two different planes, upon which pusher members 22, 22' separately and independently act. In particular, each sliding direction of pusher members 22, 22' lies on one of the respective planes on which end portion 20 is able to bend.

Figure 5:
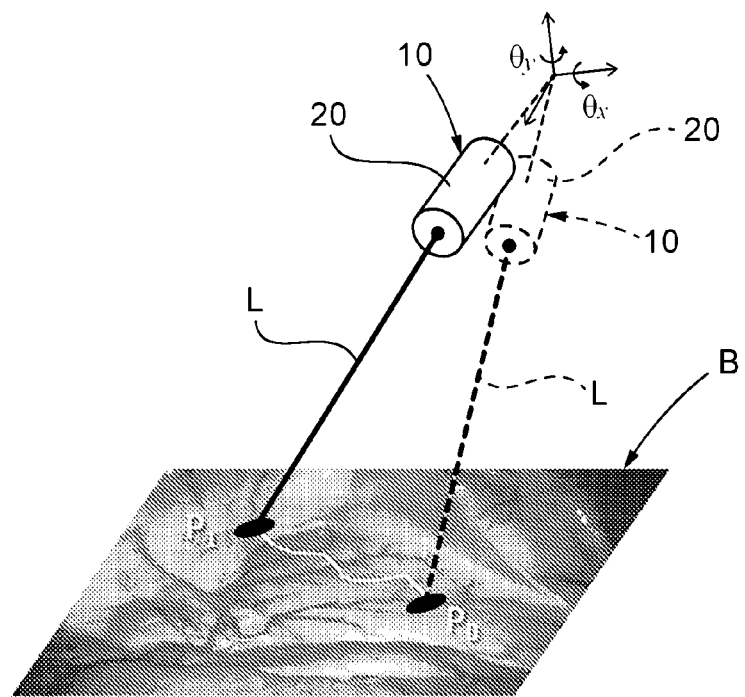
FIG. 5 is a schematic view of the module operation as shown in FIG. 4, in order to highlight its orientation abilities with respect to the patient's body.

As shown in FIG. 5, each individual action of the single pusher members 22, 22' corresponds to a specific rotation of end portion 20 relative to the longitudinal direction X-X defined by proximal portion 18 of oblong structure 12. In this way, with reference to the orientation of divergent segment 24a of waveguide 24 coming out of end portion 20, a pitch angle $\theta_x$ and a yaw angle $\theta_y$ are defined which have the desired values within a predetermined angular range relative to the longitudinal direction X-X. As shown in particular in FIG. 5, when waveguide 24 is suited to be passed through by a light beam L, said rotations are able to place this light beam L (in particular a laser beam) in whichever point of the field of action associated with module 10.

Preferably, similarly to the mono-dimensional example of the embodiment shown in FIGS. 1 to 3, the above mentioned angles $\theta_x$, $\theta_y$ can vary as explained below.

In particular, relative to the longitudinal direction X-X, pitch angle $\theta_x$ can be selected in the range between a value equal to angular sum $\gamma_x$ of an angle $\alpha_x$ (formed between end portion 20 and the longitudinal direction X-X of proximal portion 18 of oblong structure 12 in the bent condition, considering a pitching plane of end portion 20) and an angle $\beta_x$ (formed between segment 24a of outgoing waveguide 24 and the longitudinal direction Y-Y of end portion 20, considering a pitching plane of end portion 20), and a value equal to angle $\beta_x$.

In particular, relative to the longitudinal direction X-X, yaw angle $\theta_y$ can be selected in the range between a value equal to angular sum $\gamma_y$ of an angle $\alpha_y$ (formed between end portion 20 and the longitudinal direction X-X of proximal portion 18 of oblong structure 12 in the bent condition, considering a yawing plane of end portion 20) and an angle $\beta_y$ (formed between segment 24a of outgoing waveguide 24 and the longitudinal direction Y-Y of end portion 20, considering a yawing plane of end portion 20), and a value equal to angle $\beta_y$.

In this embodiment, each of the pitch and yaw angles $\theta_x$, $\theta_y$ can be selected in the range between +30°, −20° relative to the longitudinal direction X-X, independently of one another.

In particular, in a rest configuration of module 10 (in which both pusher members 22, 22' are in a retracted position) as shown in FIGS. 4, 6, 6a, 6b, waveguide 24 is arranged based on an orientation defined by a pitch angle $\theta_x$ equal to $\gamma_x$ (for example, +30°) and a yaw angle $\theta_y$ equal to $\gamma_y$ (for example, +30°).

On the other hand, in the opposite working condition of module 10 (in which both pusher members 22, 22' are in a completely extended position) as shown in FIGS. 9, 9a, 9b, waveguide 24 is arranged based on an orientation defined by a pitch angle $\theta_x$ equal to $\beta_x$ (for example, −20°) and a yaw angle $\theta_y$ equal to $\beta_y$ (for example, −20°).

In FIGS. 7, 7a, 7b, module 10 is shown in a working configuration in which only the first pusher member 22 is moved to the completely extended position, while the second pusher member 22' remains in its retracted position. This working configuration corresponds to an orientation of the outgoing segment of waveguide 24 which is defined by pitch angle $\theta_x = \beta_x$ (for example, −20°), while yaw angle $\theta_y = \gamma_y$ (for example, +30°).

On the contrary, in FIGS. 8, 8*a*, 8*b*, module 10 is shown in a working configuration in which only the second pusher member 22' is moved to the completely extended position, while the first pusher member 22 remains in its retracted position. This working configuration corresponds to an orientation of the outgoing segment of waveguide 24 which is defined by pitch angle $\theta_x=\theta_x$ (for example, +30°), while yaw angle $\theta_y=\beta_y$ (for example, −20°).

Once again with particular reference to FIG. 5, owing to the above, one can assume that if the movements of pusher members 22, 22' are actuated by motors or actuators (not shown in the drawings), which, in turn, are controlled by a control unit (also not shown), it is possible to define a predetermined path and speed for the movement between two points $P_0$ and $P_1$ located on body B of the patient towards which waveguide 24 can be oriented. In this way, in particular in case a laser beam L is used which is suited to perform a selective ablation only on a particular area of body B of the patient, it is possible to achieve maximum effectiveness and precision in the surgical activity. According to this approach, a user can initially provide the control unit with information regarding the area where the ablation is to be actually performed. Afterwards, the control unit can process parameters indicating the path and the speed of movement (and, if necessary, the intensity) of light beam L, thus controlling the movement of pusher members 22, 22' (and, in case, the actuation of a laser source associated with waveguide 24) based on said parameters. As a consequence, pusher members 22, 22' orient light beam L coming out of waveguide 24 so as to hit only the desired area where the ablation is to be performed, thus also avoiding that the part of body B subject to the procedure is excessively exposed to said light beam L.

In this embodiment, end portion 20 has an area or top 20*a* which is tapered with respect to proximal portion 18 of oblong structure 12.

Advantageously but not necessarily, pusher members 22, 22' are suited to operatively act upon end portion 20 in its area or base 20*b*. In particular, area or base 20*b* is adjacent to proximal portion 18 and located upstream of tapered area or top 20*a* of the same end portion 20.

Naturally, the principle of the present invention being set forth, the embodiments and the implementation details can be widely changed relative to what described above and shown in the drawings as a mere way of non-limiting example, without in this way going beyond the scope of protection provided by the accompanying claims.

In particular, as mentioned above and as a person skilled in the art can understand in the light of the present description, the distal scanning module is suitable for use both in diagnostic and in surgical applications. Both applications are particularly advantageous in the field of endoscopic and laparoscopic procedures, however, this should not be interpreted as limiting the scope of the present invention to these fields.

The embodiments described and shown have defined that the waveguide, in particular the optical fiber, has a divergent segment coming out of the end portion. However, in further embodiments, the waveguide can also end in the end portion, without including the divergent segment. Alternatively, the divergent segment can also, if necessary, be replaced by a divergent lens which is located on the tip of the end portion of the oblong structure and on which the outgoing waveguide converges; in this way said divergent lens can achieve an optical effect similar to the one achieved by the above mentioned divergent segment for the embodiments shown in the drawings.

Apart from what described above and shown in the drawings, the optical apparatus can comprise an image sensor associated with the end portion, in particular if the module is to be used in the field of endoscopic medical imaging. For example, it is possible to have an optical sensor or an image sensor. According to a version, the optical sensor can be connected upstream of the waveguide (and therefore located in a remote position with respect to the end portion of the oblong structure) and can detect the image transmitted through the waveguide. As an alternative to said version, the optical sensor can be associated with the top of the end portion of the oblong structure and therefore replace the waveguide; in this case the sensor can preferably be of the CCD type.

Furthermore, if the module is meant to be used in a context where there is no contact between the tip of the end portion and the target material/tissue subject to the treatment, the use of a GRIN lens (i.e. of the so-called Gradient Refractive INdex type) is optionally provided. In this case, the GRIN lens is installed on the top of the end portion of the oblong structure (downstream of the waveguide) and is therefore able to focus the light beam, in particular the laser beam. Depending on the lens used, the focusing process takes place at a specific distance from the top of the end portion. Therefore, this solution allows the light beam to be emitted and conveyed to the target in a more concentrated and dot-like manner, thus improving its precision.

As already mentioned above, in further embodiments, it is also possible to provide a solution where only the end portion (or a part thereof) is made of a material which is suited to ensure an adequate elastic return in the bent condition, while a different material is used for the proximal portion.

If possible, the technical features differentiating the different versions of the embodiments described and illustrated above can freely be exchanged among said versions and embodiments. For example, the tapering provided in the embodiment shown in FIGS. 4 to 9*c* can also be adopted for the embodiment shown in figures from 1 to 3.

The invention claimed is:

1. A distal scanning module to control aiming and movement of an optical apparatus of a diagnostic or surgical instrument; said module comprising:
   an oblong structure;
   an optical apparatus, associated with said oblong structure for facing a segment arranged inside a body cavity of a patient;
   an actuating device, for controlling a position of said oblong structure to orient said optical apparatus in said body cavity;
   wherein said oblong structure has a proximal portion and an end portion, which is at least partially deformable, so as to tend to remain in and elastically return to a bent condition, in which said end portion is normally flexed relative to said proximal portion;
   wherein said actuating apparatus comprises at least one movable pusher member, placed outside said oblong structure and which moves in a guided manner relative to said oblong structure and is suited to act upon said end portion, so as to angularly move said end portion from said bent condition towards a substantially straight condition in which said end portion is aligned with said proximal portion; and
   wherein said actuating apparatus comprises a pair of said at least one pusher member, each of the pusher members being suited to stress said end portion in a flexing manner on a respective plane and to determine a respective degree of freedom of angular movement of said end portion on said plane.

2. The module according to claim 1, wherein, in the bent condition, said end portion and a longitudinal direction defined by said proximal portion form an acute angle.

3. The module according claim 1, wherein at least said end portion of said oblong structure comprises a material provided with superelastic properties.

4. The module according to claim 3, wherein said material is a shape-memory alloy of nickel and titanium.

5. The module according to claim 1, wherein said at least one pusher member is manually movable.

6. The module according to claim 1, wherein said at least one pusher member is controllably moved by a motor or an actuator.

7. The module according to claim 1, wherein said optical apparatus comprises a waveguide, which is associated with said oblong structure.

8. The module according to claim 1, wherein said optical apparatus comprises an image sensor.

9. A distal scanning module to control aiming and movement of an optical apparatus of a diagnostic or surgical instrument; said module comprising:
- an oblong structure;
- an optical apparatus associated with said oblong structure for facing a segment arranged inside a body cavity of a patient;
- an actuating device, for controlling a position of said oblong structure to orient said optical apparatus in said body cavity;
- wherein said oblong structure has a proximal portion and an end portion, which is at least partially deformable, so as to tend to remain in and elastically return to a bent condition, in which said end portion is normally flexed relative to said proximal portion;
- wherein said actuating apparatus comprises at least one movable pusher member, placed outside said oblong structure and which moves in a guided manner relative to said oblong structure and is suited to act upon said end portion, so as to angularly move said end portion from said bent condition towards a substantially straight condition in which said end portion is aligned with said proximal portion;
- wherein said optical apparatus comprises a waveguide, which is associated with said oblong structure; and
- wherein the waveguide ends, in correspondence to said end portion, with an optically divergent segment that is optically divergent relative to a longitudinal direction of said end portion; said optically divergent segment being inclined, in a direction that is opposite to the direction in which said end portion is inclined, relative to the longitudinal direction defined by said proximal portion, when said end portion is in the bent condition.

10. The module according to claim 9, wherein said optical apparatus comprises an image sensor.

\* \* \* \* \*